United States Patent [19]

Bastasz et al.

[11] Patent Number: 4,782,302
[45] Date of Patent: Nov. 1, 1988

[54] DETECTOR AND ENERGY ANALYZER FOR ENERGETIC-HYDROGEN IN BEAMS AND PLASMAS

[75] Inventors: Robert J. Bastasz, Livermore, Calif.; Robert C. Hughes; William R. Wampler, both of Albuquerque, N. Mex.

[73] Assignee: The United States of America as represented by the United States Department of Energy, Washington, D.C.

[21] Appl. No.: 925,590

[22] Filed: Oct. 31, 1986

[51] Int. Cl.$^4$ .................. G01N 27/40; G01N 27/12
[52] U.S. Cl. .................. 324/71.3; 324/71.5; 357/25
[58] Field of Search .............. 340/634; 73/23; 204/1 T; 357/25; 324/71.3, 71.4, 71.5; 250/305, 337, 363 SG

[56] References Cited

U.S. PATENT DOCUMENTS

| | | |
|---|---|---|
| 3,479,257 | 11/1969 | Shaver . |
| 3,507,145 | 4/1970 | Loh . |
| 3,636,417 | 1/1972 | Kimura . |
| 4,014,109 | 3/1977 | Schramm ............... 250/363 SG |
| 4,030,340 | 6/1977 | Chang . |
| 4,058,368 | 11/1977 | Svensson .................. 357/25 |
| 4,095,114 | 6/1978 | Taumann ................. 250/305 |
| 4,324,760 | 4/1982 | Harris . |
| 4,324,761 | 4/1982 | Harris ..................... 324/71.5 |
| 4,373,375 | 2/1983 | Terhune ..................... 73/23 |
| 4,398,344 | 8/1983 | Gould . |
| 4,457,161 | 7/1984 | Iwanaga .................. 340/634 |
| 4,481,499 | 11/1984 | Arima . |
| 4,506,157 | 3/1985 | Keller .................... 250/337 |
| 4,512,870 | 4/1985 | Kohara .................... 357/25 |
| 4,563,249 | 1/1986 | Hale ...................... 204/1 T |
| 4,586,143 | 4/1986 | Kaneyasu ................ 340/634 |
| 4,638,443 | 1/1987 | Kaneyasu ................ 340/634 |
| 4,668,374 | 5/1987 | Bhagat .................... 357/25 |

OTHER PUBLICATIONS

Kusser: "Investigation into the Mechanism of the Catalized Phase Boundary Reaction of Hydrogen with Palladium . . . ", Z. fur Electrochemie—pp. 675-679 (1962).
Lundstrom: "Hydrogen Sensitive MOS-Structures"—Sensors & Actuators, 403-426 (1981).
Ruths: "A Study of Pd/Si MIS Schottky Barrier Diode Hydrogen Detector"—IEEE Trans. Electron Devices—1003-1009 (1981).

*Primary Examiner*—Reinhard J. Eisenzopf
*Assistant Examiner*—Jose M. Solis
*Attorney, Agent, or Firm*—Armand McMillan; James H. Chafin; Judson R. Hightower

[57] ABSTRACT

A detector for detecting energetic hydrogen ions and atoms ranging in energy from about 1 eV up to 1 keV in an evacuated environment includes a Schottky diode with a palladium or palladium-alloy gate metal applied to a silicondioxide layer on an n-silicon substrate. An array of the energetic-hydrogen detectors having a range of energy sensitivities form a plasma energy analyzer having a rapid response time and a sensitivity for measuring fluxes of energetic hydrogen. The detector is sensitive to hydrogen and its isotopes but is insensitive to non-hydrogenic particles. The array of energetic-hydrogen detectors can be formed on a single silicon chip, with thin-film layers of gold metal applied in various thicknesses to successive detectors in the array. The gold layers serve as particle energy-filters so that each detector is sensitive to a different range of hydrogen energies.

5 Claims, 3 Drawing Sheets

DETECTOR AND ENERGY ANALYZER FOR ENERGETIC-HYDROGEN IN BEAMS AND PLASMAS

The U.S. Government has rights in this invention pursuant to Contract No. DE-AC04-76DP00789 between the U.S. Department of Energy and AT&T Technologies, Inc.

FIELD OF THE INVENTION

The present invention relates to the field of detectors for plasmas, and more particularly to detectors for low energy plasmas of hydrogen and its isotopes.

BACKGROUND OF THE INVENTION

In the art of characterizing ion beams and/or plasmas there is a need for a detector of ions and neutral atoms of hydrogen and its isotopes that have kinetic energies ranging from about 1 eV to about 1 keV. There is also a requirement to quantify the flux (i.e., particles per unit area per unit time; e.g., H atoms/cm$^2$-sec) of hydrogen emanating from low-energy beams and/or plasmas. Here low-energy is meant to mean any particle kinetic energy below about 10 keV (kilo electron Volts). Detection and measurement of energetic-hydrogen in low-energy beams and/or plasmas is needed to monitor the behavior of fusion energy devices and plasma deposition processes.

It would also be desirable to have an energetic-hydrogen detector that is selectively sensitive to the hydrogen isotopes (i.e., hydrogen, deuterium, and tritium ions and atoms) and relatively insensitive to non-hydrogenic particles.

It would also be desirable to have a plasma detection means that provides an energy analysis of the particles emanating from a plasma; that is, an analysis of the plasma flux as a function of particle energy.

Prior art includes the use of a Schottky barrier diode sensor for detecting the presence of molecular hydrogen, not energetic hydrogen, under ambient pressure and above ambient pressure conditions.

The aforesaid molecular hydrogen sensor has a very slow response time (up to tens of minutes). Such a long response time would not be tolerable in a plasma hydrogen environment where a much shorter response time would be required for measuring energetic hydrogen.

SUMMARY OF THE INVENTION

Accordingly, it is a primary object of the present invention to provide a detector that detects the presence of low energy plasma particles in a high vacuum environment.

Another object of the invention is to provide a low energy plasma detector that permits quantitative measurement of flux of particles emanating from a plasma.

Another object is to provide a plasma detection means that provides an energy analysis of a plasma.

Still another object of the invention is to provide a Schottky barrier diode plasma sensor which operates satisfactorily at low pressures in a high vacuum.

An additional object of the invention is to provide a plasma sensor which has a rapid response time.

Yet another object of the present invention is to provide an energetic hydrogen detector that integrates exposure to hydrogen plasma so that when the source of hydrogen plasma is cut off or depleted, the sensor continues to provide a measurement of prior cumulative exposure to the plasma.

Still another object of the invention is to provide a plasma detector which is sensitive to plasmas of hydrogen, deuterium, and tritium and insensitive to other plasma particles.

Additional objects, advantages, and novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved plasma detection apparatus and method are provided. A plasma detector made in accordance with the invention includes a Schottky barrier diode. Generally, a metal-oxide-semiconductor (MOS) receives a deposit of a metal such as palladium to form the Schottky barrier diode. Preferably, a silicon substrate is treated to have a thin layer of silicon dioxide. A metal, such as palladium, is deposited on the silicon dioxide layer, to form the Schottky barrier diode. Then an additional layer, which serves as a high-pass, energetic-particle filter, is deposited atop the previous metal layer. The thickness and content of the plasma filter layer is selected in accordance with the particle energy that is to be detected by the plasma detector. The plasma detector of the invention operates in an evacuated environment.

In accordance with another aspect of the invention, a plurality of plasma detectors are grouped in an array of detectors. Each of the individual plasma detectors in the array is selected for its optimum response to a particular set of energies. The filter material acts such that only particles with sufficient kinetic energy, i.e., those whose projected range is greater than the thickness of the filter layer, can pass through the filter layer and reach the sensing junction of the diode. By having each detector in the array responsive only to hydrogen particles above a distinct kinetic energy, the array of detectors provides a plasma energy analyzer.

In accordance with another aspect of the invention, a method is provided for measuring energetic hydrogen and its isotopes in an evacuated environment. The method involves exposing a plasma detector of the invention, namely a Schottky barrier diode based detector, to the plasma in the evacuated environment. The plasma detector of the invention preferably includes: a silicon substrate; a silicon dioxide layer on the substrate; and a layer of gate metal deposited on the silicon dioxide layer. The gate metal is selected from the group consisting of palladium and alloys of palladium and silver. The plasma detector further includes a first conductor connected to the gate metal and a second conductor connected to the silicon substrate.

Still other objects of the present invention will become readily apparent to those skilled in this art from the following description, wherein there is shown and described a preferred embodiment of this invention. Simply by way of illustration, the invention will be set forth in part in the description that follows and in part will become apparent to those skilled in the art upon examination of the following or may be learned with the practice of the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF A PREFERRED EMBODIMENT OF THE INVENTION

Although the phenomena occurring within the plasma sensor of the invention are not fully understood, a theoretical explanation is provided herein in order to lend greater understanding as to the operation of the invention.

Figure 1:
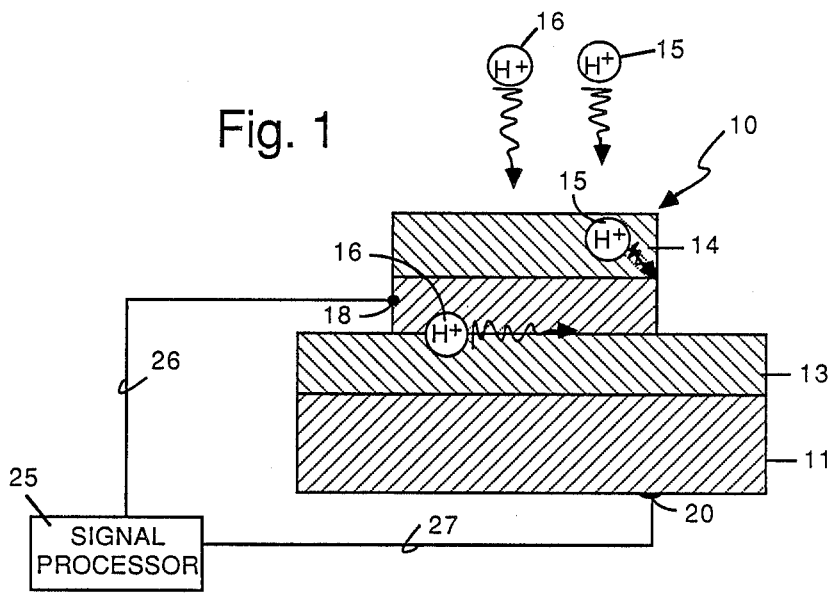
FIG. 1 shows a cross sectional view of an idealized energetic hydrogen sensor of the invention.

With reference to the drawings, and more particularly to FIG. 1, there is disclosed a preferred embodiment of a energetic-hydrogen detector 10 of the present invention. The energetic-hydrogen detector 10 is a Schottky barrier diode allowing current to flow in one direction through the schottky barrier. The energetic-hydrogen detector is comprised of a silicon substrate 11, a layer of silicon dioxide 12, a palladium layer 13, and a gold filter layer 14. The gate of the Schottky barrier diode is formed at the interface between the palladium layer 13 and the silicon layer 11. For illustration, two types of low energy hydrogen ions are shown, i.e., hydrogen ions having an energy of 50 eV are shown as elements 15 with relatively short tails whereas hydrogen ions having an energy of 1 kev are shown as elements 16 with relatively long tails.

In FIG. 1, the gold filter layer 14 successfully stops the lower-energy 50 eV hydrogen ions and allows the higher energy 1 keV. hydrogen ions to pass through it. The 1 keV hydrogen ions which pass through the filter layer 14 then diffuse through the palladium layer 13 and reach the interface between the palladium and the silicon dioxide. Although the hydrogen is not believed to diffuse through the silicon dioxide layer 12, it exerts an electrostatic effect upon the silicon-dioxide-silicon interface and thereby exerts an influence upon the reverse-bias current through the gate of the plasma sensor 10.

The energetic-hydrogen detector 10 of the invention operates satisfactorily over a range of vacuum conditions ranging from $1 \times 10^{-4}$ Torr down to at least $1 \times 10^{-9}$ Torr (the base pressure of the present vaccuum system). The ion source that was used for test and evaluation of the plasma sensors of the invention was a Colutron ion source which produces monoenergetic ion beams by mass analysis and focussing into beams about 200 microns in diameter. The ion beams were rastered over the active area of the energetic-hydrogen sensor of the invention at a 0.2 microampere current.

The energetic-hydrogen detector 10 of the invention is connected to electrical signal processing apparatus 25 by means of first contact 18 and second contact 20 and respective conductors 26 and 27. The first contact 18 can be an electrical conductor which is adhesively bonded to the gate metal 13 by means of a silver loaded epoxy adhesive. A microscope can be used to aid in the attachment of the first contact. The second contact 20 is an ohmic contact attached to the bottom of the silicon substrate 11.

With a 30 nm palladium alloy (90% palladium and 10% silver) forming the gate metal layer 13, short exposures ($1 \times 10^{13}$ ions over a 0.02 cm² area) to hydrogen ion beams at 1 keV were easily detected by the increase in reverse-bias current through the energetic-hydrogen detector 10 at 25 degrees C. The response of the detector 10 was surprisingly and unexpectedly nearly instantaneous with respect to the time scale of the measuring procedure which required approximately one second to switch from monitoring the ion flux from the ion source to monitoring the response of the detector. In all cases, the projected range of the ions was less than half the thickness of the metal layer. The response of the detector 10 approached 100 microamperes for a cumulative hydrogen ion dose of 2 microCoulombs. The hydrogen ions are cumulatively measured by the plasma sensor of the invention; thus the plasma sensor of the invention is dosimetric. It is believed that the plasma protons are cumulatively or dosimetrically measured by the plasma sensor of the invention because the protons become trapped at the palladium/silicon dioxide interface. Exposures to cumulative plasma exposure of larger than about 4 microCoulombs caused the detector response to reach saturation.

A possible explanation is offered as to why the surprising and unexpected rapid response of the plasma sensor of the invention occurs. For molecular hydrogen to be measured by a Schottky barrier sensor, the molecular hydrogen must undergo a two step interaction with the sensor. First, the molecular hydrogen must adsorb on the surface and dissociate into atomic hydrogen atoms. Next, the hydrogen atoms diffuse in the palladium of the Schottky barrier diode to reach the palladium/silicon dioxide interface. The adsorption and dissociation step takes a relatively long period of time, whereas the diffusion step is relatively instantaneous at 25 degrees C. When energetic hydrogen is implanted, there is no need for the slow dissociation step to occur. The hydrogen will rapidly diffuse into the palladium to reach the palladium/silicon dioxide interface.

Not only is the response of the plasma detector of the invention nearly instantaneous and not only does the plasma detector of the invention serve to provide a cumulative measurement of exposure to energetic hydrogen, but the plasma detector of the invention provides a surprising and unexpected long term decay of the residual reverse-bias current. A 10% reduction in reverse-bias current in vacuum at 25 degrees C requires nearly $2 \times 10^4$ seconds. Thus, the reading of the sensor can be taken at a considerable time after the sensor has undergone exposure to energetic hydrogen.

Figure 2:
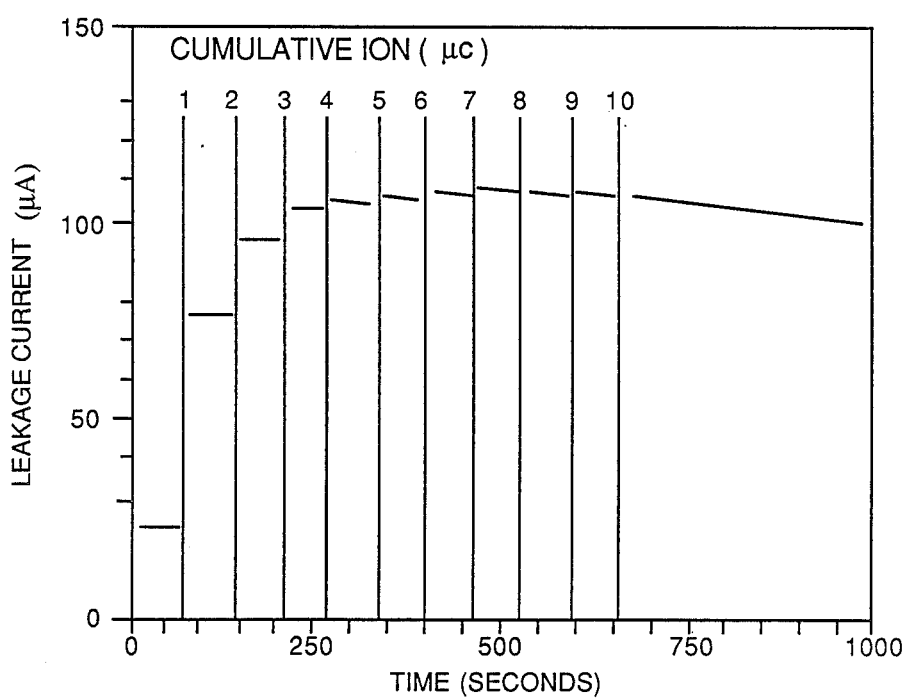
FIG. 2 shows a graph of the electrical response of a sensor of the invention with respect to time and particle influx.

More particularly, FIG. 2 shows a graph of the reverse-bias leakage current (in microamperes) versus time (in seconds) for an energetic hydrogen sensor of the invention when exposed to a hydrogen ion beam. The beam consisted of 2 keV hydrogen ions. The sensor of the invention was biased to 0.5 V and its leakage current was monitored following successive 1 micro- Coulomb ion beam exposures which are indicated in FIG. 2 by the vertical lines numbered 1–10. After the last exposure, the current was observed to decay very slowly at 25 degrees C.

If desired, the time required to reduce reverse-bias current in the sensor can be greatly shortened by heating the sensor to 100–150 degrees C for a few seconds. The reverse-bias current falls rapidly to within 20% of its initial value upon cooling back to 25 degrees C. A long term decay of the residual reverse-bias current after heating was observed and appears to have an exponential time dependence. It was also found that exposure of the energetic-hydrogen to gaseous oxygen further reduces the reverse-bias current. After a heating-/cooling cycle, the sensitivity of the sensor to energetic hydrogen was restored, and the response curve could be reproduced to within 5% of the earlier response.

Figure 3:
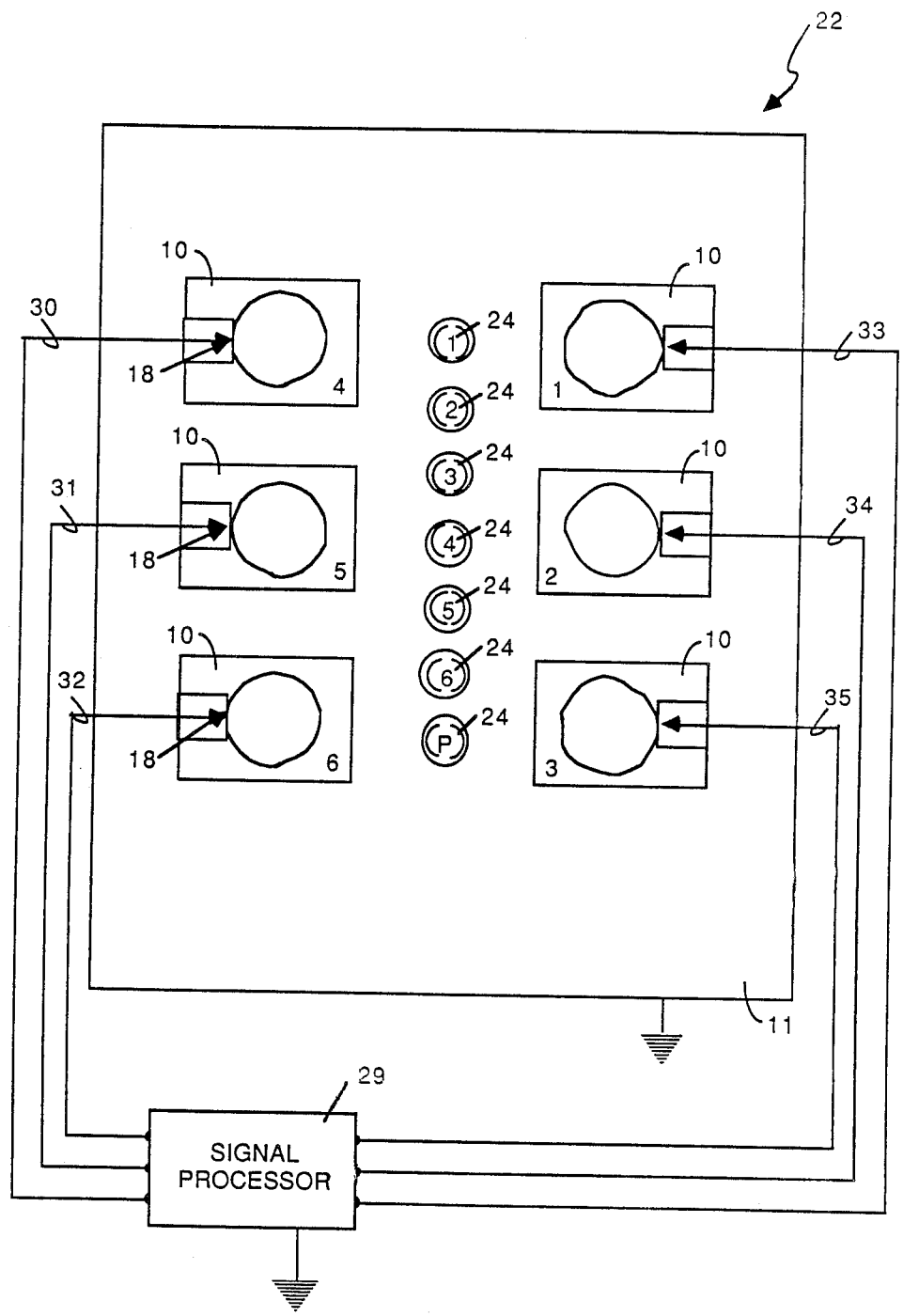
FIG. 3 shows schematic view of a energy spectrum analyzer of the invention.
Figure 4:
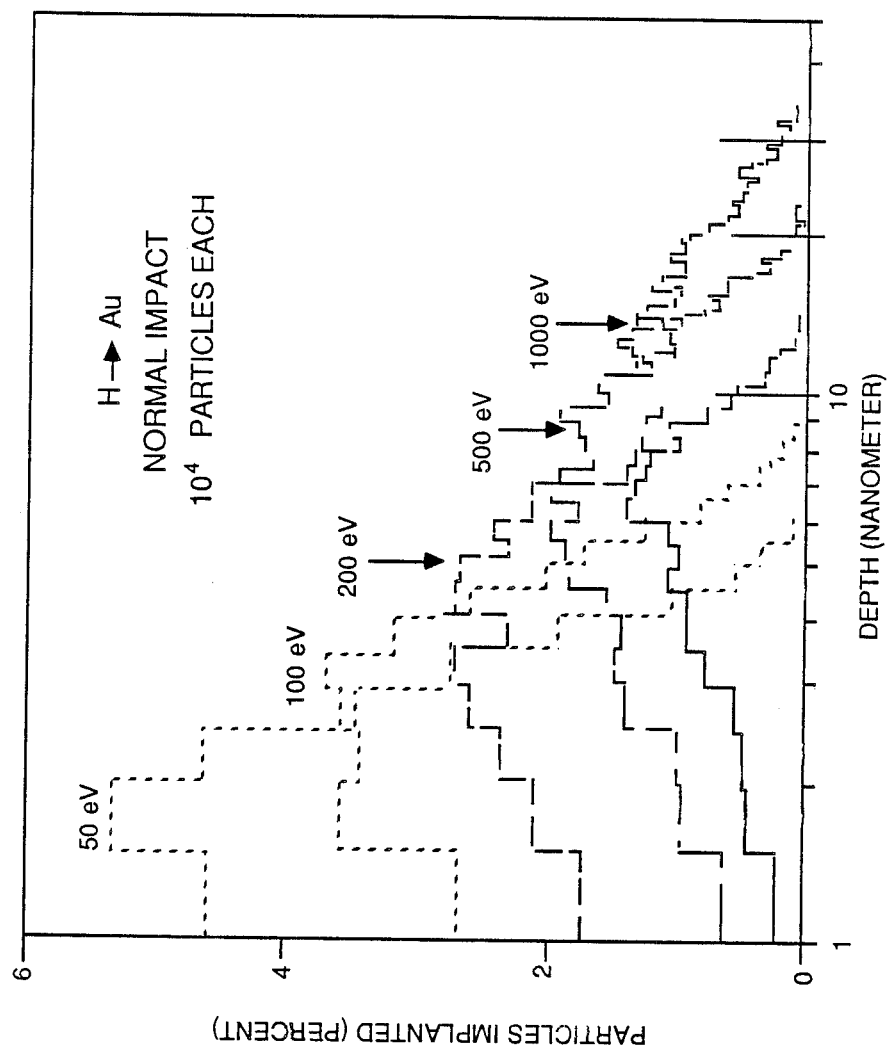
FIG. 4 shows a graph of the relationship between the kinetic energy of impacting hydrogen ions and the thickness of gold film used to filter hydrogen ions in a plasma energy analyzer of the invention.

Another aspect of the invention is depicted in FIGS. 3 and 4. A plurality of individual sensors 10 are arrayed on a single silicon chip 11 to form a plasma energy analyzer 22 which occupies a space approximately 3 millimeters across. In FIGS. 3, the plasma energy analyzer 22 includes six energetic-hydrogen sensors 10. The array of sensors forming the plasma energy analyzer can be fabricated by the following procedure. First, the silicon substrate is cleaned in hot trichloroethylene followed by rinsing in acetone. Just prior to being placed in a vacuum system for vacuum deposition of the gate metal, the silicon is washed in hot propanol followed by blow drying with ultra high purity nitrogen gas. A shadow mask design is employed to make an array of six diodes on a single silicon chip whose overall dimensions are on the order of a few millimeters. Each diode is about 400 microns in diameter. There are alignment structures 24 in the center of the chip that are used for alignment of the shadow mask for depositing the gas sensitive metal layer on the chip. The chip is fabricated from n-type silicon, and it has a very thin silicon dioxide layer on the upper surface. The silicon dioxide layer can be grown on the surface of the silicon by thermal oxidation. For example, n-silicon can be oxidized at 650 degrees C in oxygen gas. The thickness of the silicon dioxide layer is typically on the order of 15 to 30 Angstoms. The gate metal such as palladium or a palladium/silver alloy is then deposited on the silicon dioxide layers by any conventional technique such as by vacuum deposition. At this point in the process, an array of Schottky diodes has been made. After making the array of diodes, each diode is selectively deposited with a different thickness of gold film which serves as filter material for energetic hydrogen. A very thin layer of gold film will filter out particles having very low energy and prevent incident hydrogen ions or atoms with very low energy from reaching the palladium/silicon dioxide interface of the respective sensor. A thicker film of gold on another sensor will filter out particles having a higher energy. A still thicker film of gold on yet another sensor will filter out particles of still higher energy. In the array of sensors, each sensor will have a film of gold at a different thickness and will, therefore, be sensitive to energetic hydrogen above a different energy threshold. In this way, the array of energetic hydrogen sensors serves as a plasma energy analyzer. Each of the six sensors 10 in the array 22 has a first contact 18 which is connected to a siz channel signal processor 29 by respective conductors 30–35. Both the array 22 and the signal processor 29 are also connected to an electrical ground.

To accomplish deposition of an increasingly thicker gold film deposit on respective sensors, a series of masks are placed over the diode array in succession to enable build up of gold layers on selected diodes with exclusion of film build up on other diodes. More specifically, the first mask for the gold filter film may permit five diodes to receive gold deposition with one diode excluded. A second mask may permit four diodes to receive gold deposition with two diodes excluded. A third mask may permit three diodes to be treated with three excluded. This procedure would be repeated until the last mask whereby one diode would be treated with five diodes excluded. By following this procedure, each diode in the array would have a different thickness of gold filter deposited thereon.

An alternate procedure for depositing the gold films on the diodes would be simply to mask out five diodes and conduct an exclusive deposition process for only one selected diode at a time. This procedure would be repeated until each diode received its separately applied filter film.

In FIG. 4, a graph is shown which depicts the relationship between the thickness or depth of the gold filter film and the ability of the film to filter out hydrogen ions or atoms of varying energy that impact on the films. The vertical axis of the graph represents the percent of hydrogen that is implanted in the gold; that is, filtered out by the gold film. The horizontal axis of the graph represents the depth of the gold filter film. Profiles for hydrogen at the following energies are depicted in FIG. 4: 50 ev; 100 ev; 200 ev; 500 ev; and 1000 ev. It is clear from FIG. 4 that relatively low energy hydrogen is absorbed by thinner layers of gold filter film. To filter the higher energy hydrogen, thicker layers of gold filter are needed.

In summary, numerous benefits have been described which result from employing the principles of the invention. The invention provides a low energy hydrogen detector. The invention also provides an array of low energy hydrogen detectors which serve as a plasma energy analyzer. The hydrogen detector of the invention is sensitive to energetic hydrogen and is insensitive to non-hydrogenic particles. The hydrogen sensor of the invention has a very rapid response time and retains cumulative hydrogen dose readings for a relatively long period of time. The sensor of the invention works well in a high vacuum environment.

The foregoing description of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

Although the preferred embodiments of the invention have been disclosed as utilizing a silicon substrate, other semiconductor substrates may also be employed.

Other filter materials besides the gold layer may also be used for plasma filters. For example, organic materials containing double or triple covalent bonded carbons may also be used as plasma filter materials. Additionally, other elements that trap hydrogen, form hydrides, or in which hydrogen has a low-diffusion rate may also be used as filter materials.

The gate metal can be composed of a pure metal such as palladium or can be a metal alloy. Another suitable alloy, in addition to the alloy disclosed above, is 95% palladium and 5% silver.

The number of Schottky diode energetic-hydrogen sensors of the invention than can be arrayed in a plasma energy analyzer can be any desired number that is practical in terms of the space occupied by the diodes on the semiconductor chip. The more diodes that are used with different energy filtering characteristics, the greater the resolution of the energy analyzer.

An array of diodes with or without a plasma filtering layer can be used to obtain plasma energy information in a two or three dimensional array in a relatively large spatial area or region to provide information as to the spatial distribution of plasma in the area or region. For example, a thousand hydrogen sensors could be incorporated onto one chip and provide spatial information with respect to the plasma measured. With a large array of diodes on a single chip, it would be desirable to incorporate onto the chip on-board signal processing so that various multiplexing functions can be taken care of locally on the chip so that a thousand wires would not have to come out of the chip. The plasma sensors of the invention can be used as hydrogen flux sensors for sensing energetic hydrogen particles escaping from hydrogen plasmas such as in a fusion reactor or device.

The energetic-hydrogen sensors of the invention can also be used as a general diagnostic apparatus with ion beam instruments to evaluate beam flux distribution and the distribution of the energy of the beam in space.

The energetic-hydrogen sensors of the invention are also useful for diagnosing neutral particle beams. The sensing mechanism of the detector does not require the incident particles to have charge, so the sensor can be used to measure neutral hydrogen atomic particles. Similarly, an array of sensors of the invention can be used for measuring an energy distribution of neutral atomic hydrogen particles.

What is claimed is:

1. A plasma or beam energy spectrum analyzer, comprising:
   a plurality of energetic-hydrogen sensors selectively responsive to hydrogen ions and atoms of different kinetic energies in a plasma or a beam, said sensors providing electrical signals, and
   means for processing the signals from said sensors to provide an energy analysis of the hydrogen ions and atoms in a plasma or beam.

2. The energy spectrum analyzer of claim 1 wherein each said energetic-hydrogen sensor has a filter layer of different thickness for providing energy-selective detection of energetic hydrogen.

3. The plasma energy spectrum analyzer described in claim 2 wherein said filter layers are comprised of gold metal.

4. The energy spectrum analyzer described in claim 1 wherein said energetic-hydrogen sensors are comprised of:
   a silicon substrate;
   a silicon dioxide layer on said subsrate;
   a layer of gate metal deposited on said silicon dioxide layer, said gate metal selected from the group consisting of palladium and alloys of palladium and silver;
   in all but one sensor, a filter layer comprising gold metal which is of different thickness for each sensor;
   first conductor means connected to said gate metal layers; and second conductor means connected to said silicon substrate.

5. The plasma energy spectrum analyzer described in claim 1 wherein said energetic-hydrogen sensors are Schottky barrier diode devices.

* * * * *